United States Patent
Kokubun et al.

(10) Patent No.: US 7,006,593 B2
(45) Date of Patent: Feb. 28, 2006

(54) METHOD OF PRODUCING CARDIAC TOMOGRAM AND TOMOGRAPH USING X-RAY CT APPARATUS

(75) Inventors: Hiroto Kokubun, Kashiwa (JP); Tetsuo Nakazawa, Kashiwa (JP); Osamu Miyazaki, Moriya (JP)

(73) Assignee: Hitachi Medical Corporation, Tokyo (JP)

(*) Notice: Subject to any disclaimer, the term of this patent is extended or adjusted under 35 U.S.C. 154(b) by 77 days.

(21) Appl. No.: 10/496,420

(22) PCT Filed: Nov. 28, 2002

(86) PCT No.: PCT/JP02/12448

§ 371 (c)(1),
(2), (4) Date: May 21, 2004

(87) PCT Pub. No.: WO03/045247

PCT Pub. Date: Jun. 5, 2003

(65) Prior Publication Data

US 2005/0069081 A1    Mar. 31, 2005

(30) Foreign Application Priority Data

Nov. 30, 2001  (JP)  ............................. 2001-366017

(51) Int. Cl.
*A61B 6/03* (2006.01)
(52) U.S. Cl. .............................. 378/8; 378/15; 378/901
(58) Field of Classification Search .................... 378/4, 378/8, 15, 901
See application file for complete search history.

(56) References Cited

U.S. PATENT DOCUMENTS

| | | | |
|---|---|---|---|
| 2004/0077941 A1* | 4/2004 | Reddy et al. | 600/428 |
| 2005/0175143 A1* | 8/2005 | Miyazaki et al. | 378/19 |

FOREIGN PATENT DOCUMENTS

| | | |
|---|---|---|
| JP | 2000023969 | 1/2000 |
| JP | 2000051208 | 2/2000 |
| JP | 2000107174 | 4/2000 |
| JP | 2001137232 | 5/2001 |
| JP | 2002011001 | 1/2002 |
| JP | 2002325758 | 11/2002 |

* cited by examiner

*Primary Examiner*—David V Bruce
(74) *Attorney, Agent, or Firm*—Cooper & Dunham LLP

(57) ABSTRACT

In an X-ray CT apparatus having a multi-slice detector, the retrospective ECG (Electrocardiography) gating imaging is applied to helical scans. Discontinuity of projection data generated in the scans is interpolated using data at a heartbeat time phase in 180-degree opposite relation to reduce motion artifacts. Further, projection data at an arbitrary slicing position and in at arbitrary heartbeat time phase are formed utilizing continuous divided projection data obtained above, and by properly combining or gathering them, a tomogram of whole heart, a three-dimensional image thereof, and further, a three-dimensional cardiac moving image in heartbeat time phases with an arbitrary time interval can be continuously and smoothly created.

28 Claims, 11 Drawing Sheets

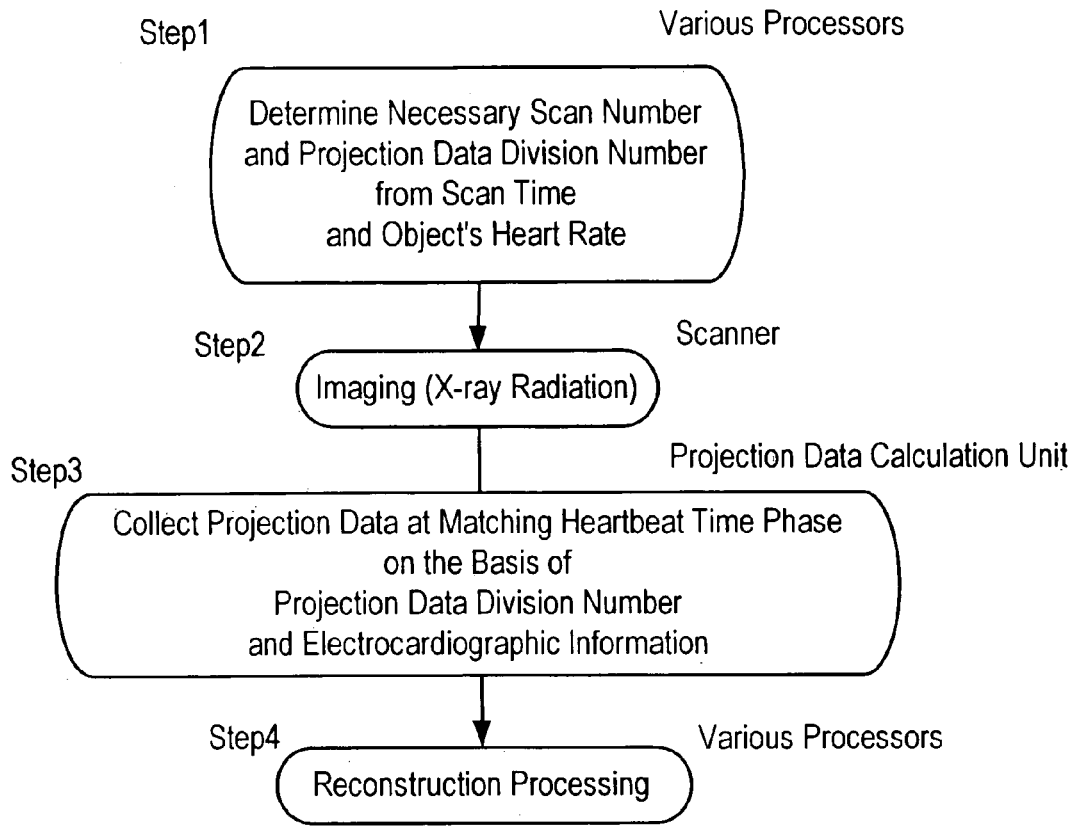
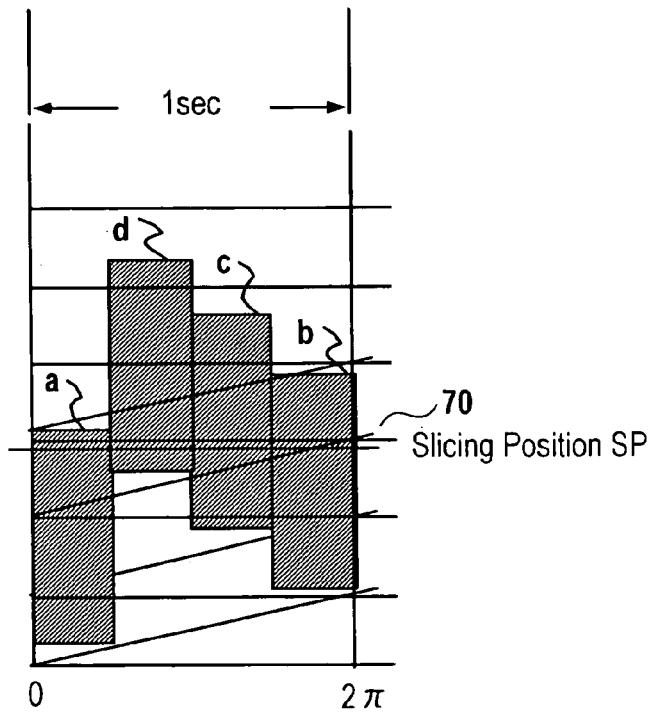

110 Discontinuous Portion of Projection Data

Z-Axis Direction 0    2π
Projection Angle Direction

180-Degree Opposite Relation

Slicing Position SP1
Slicing Position SP2

Discontinuous Portion A
Discontinuous Portion B 0  2/5π  4/5π  6/5π  8/5π  2π

Embedding of Projection Data Formed by Opposite Data

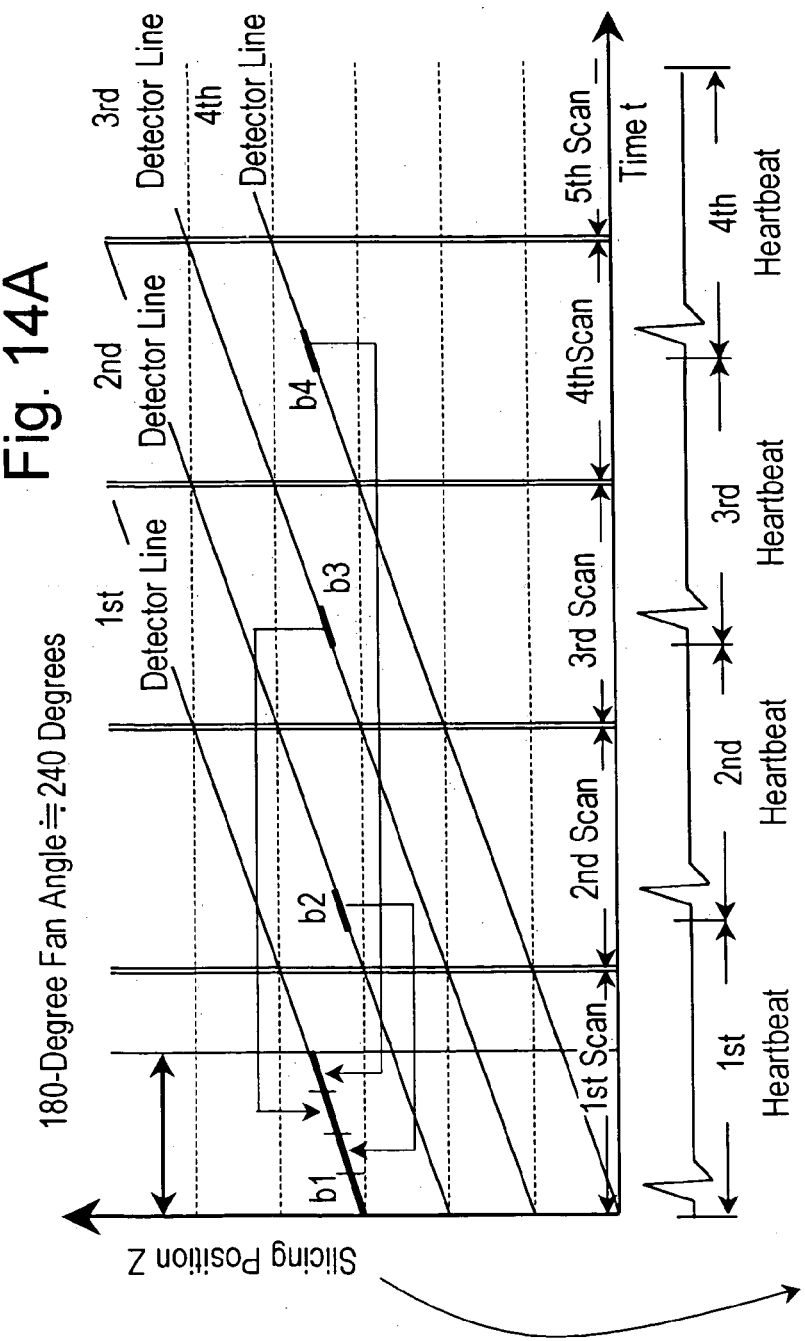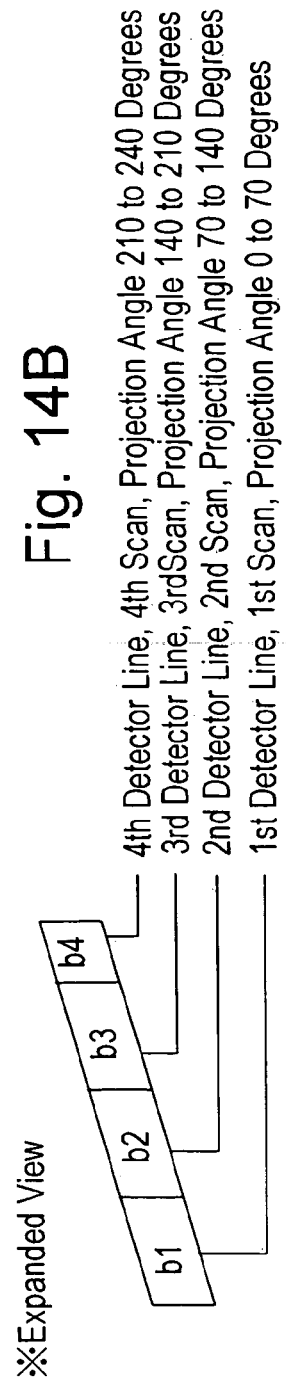

METHOD OF PRODUCING CARDIAC TOMOGRAM AND TOMOGRAPH USING X-RAY CT APPARATUS

TECHNICAL FIELD

The present invention relates to a method of producing a cardiac tomogram and tomograph using an X-ray CT apparatus, more particularly to a method and apparatus for creating a cardiac tomogram by applying a retrospective ECG (electrocardiography) gating imaging method to an X-ray CT apparatus which performs helical scan and detects projection data with a multi-slice detector.

BACKGROUND OF THE INVENTION

Generally, when a heart of human body is imaged by an X-ray CT apparatus, the image is diagnostically undesirable when motion artifacts appear on the tomogram due to its heartbeat. To prevent motion artifacts from being generated, it is necessary to highly speed up scanning over one heartbeat cycle to a speed of one heartbeat cycle or less. However, heart rates depend on individual bodies, and physical and mental conditions at the point of imaging in the same body. With a scanner mechanism of the current third-generation CT system, it is hard to highly raise its scan speed to a speed of all heartbeat cycles or less. Therefore, a method is disclosed in Japanese Unexamined Patent Publication 2001-137232 in which an object is imaged not in synchronism with the heartbeat cycle, and data at the same heartbeat time phase are combined after acquiring projection data to reconstruct an image. In this method, electrocardiographic cycle of the object is measured, projection data are acquired by scanning the heart of the object at an angular rate desynchronized with the measured electrocardiographic cycle, and a tomogram of the object's heart is created from segments of temporally discontinuous projection data. The image thus created corresponds to a portion which is selected in the electrocardiographic cycle, e.g., a relatively stationary portion.

However, in the method of producing a cardiac tomogram disclosed in Japanese Unexamined Patent Publication 2001-137232, the following two points are not mentioned.

One is that in some cases a discontinuous portion is generated in projection data necessary for image reconstruction in a longitudinal direction (slicing direction) of the object because in the X-ray CT apparatus having a multi-slice X-ray detector, helical scans are performed, i.e., imaging is performed while an X-ray source and the X-ray detector are transferred and rotated around the object, and temporally discontinuous data are corrected in a projection angle direction (view direction). When the projection data for image reconstruction includes a discontinuous portion, the projection data of a desired slicing position come short. Accordingly, if an image is reconstructed with those data, artifacts are generated on the image or the image quality is significantly deteriorated.

The other one is that when phases of a heartbeat cycle and of a scan cycle are different, the number of data necessary for reconstruction in a projection angle direction it too small to make a reconstruction image and so the image cannot be reconstructed in some cases.

Moreover, when conditions of heartbeat is generally observed, scanning time is conventionally fine-adjusted so that the scan cycle is synchronized with the heartbeat cycle, and cardiac tomograms disclosed in the above Japanese Unexamined Patent Publication 2001-137232 or three-dimensional images obtained from a plurality of cardiac tomograms are sequentially displayed in order of time phase of heartbeat as a moving image. However, in consideration of mechanical accuracy of the scanner which rotates the X-ray source and the X-ray detector around the object, there is a limit on the range of fine adjustment of scanning time. Further, according to the above conventional techniques, one heartbeat is divided and a moving image is produced from images obtained at each heartbeat time phase, thereby it is hard to make a smooth moving image.

Therefore, an object of the present invention is to provide a method of producing a cardiac tomogram and tomograph which can eliminate the discontinuous portion of projection data in the slicing direction and obtain a cardiac tomogram at an arbitrary slicing position with reduced motion artifact caused by heartbeat even when helical scans are performed with an X-ray CT apparatus having a multi-slice detector.

Further, another object of the invention is to provide a method of producing a cardiac tomogram and tomograph which can obtain a cardiac tomogram with few motion artifacts caused by heartbeat and a smoother moving image of cardiac section by solving lack of data number in the projection angle direction necessary for reconstruction even when difference is generated between phases of heartbeat cycle and of scan cycle.

SUMMARY OF THE INVENTION

To solve the above-stated objects, a method of producing cardiac tomogram using an X-ray CT apparatus according to the invention, in which helical scans are performed with an X-ray CT apparatus having X-ray detectors aligned in multiple lines in a slicing direction of an object to be examined and a cardiac tomogram of the object is created using projection data detected by the X-ray detector, includes the steps of: measuring electrocardiographic information of the object; calculating division number of projection data necessary for reconstruction of a tomogram in each scan of the helical scans; collecting divided projection data at an identical heartbeat time phase on the basis of the division number of projection data and the electrocardiographic cycle obtained in the step of measuring the electrocardiographic information, and forming projection data necessary for reconstruction of a tomogram; compensating for a discontinuous portion of the above-formed projection data in the slicing direction of the object and forming continuous projection data; and creating a cardiac tomogram of the object using the continuous projection data. The step of calculating the division number of projection data includes a step of finding the scanning number at which a scan cycle of helical scans is in synchronism with an electrocardiographic cycle obtained from the electrocardiographic information and calculating the division number of projection data necessary for reconstruction of a tomogram in each of the synchronizing scans.

The step of forming the continuous projection data includes interpolating means for interpolating the discontinuous portion of the projection data in the longitudinal direction of the object with projection data in 180-degree opposite relation and at an identical heartbeat time phase, or interpolating means for interpolating using projection data of a portion at the same heartbeat time phase in the vicinity of the discontinuous portion, and forms projection data which is continuous in the longitudinal direction of the object with the interpolating means. The projection data used in the interpolation utilizing the projection data at the same heartbeat time phase in the vicinity of the discontinuous portion may be data obtained by weighing the projection data at the same heartbeat time phase in the vicinity of the discontinuous portion.

Since the discontinuity in the projection data generated in the helical scans can be solved by the above method of producing a cardiac tomogram, a cardiac tomogram with few motion artifacts caused by heartbeat and good image quality can be obtained.

Further, the step of forming the continuous projection data includes a step of finding data width of the divided projection data, and forms the projection data at the arbitrary heartbeat time phase and in the range of projection angle necessary for image reconstruction by adjusting at least any of a starting projection angle of the divided projection data, the number of the divided projection data, and the data width.

The projection data in the range of projection angle necessary for image reconstruction also may be formed by setting the data width of the divided projection data to be wide, performing weighing processing on the data close to boundaries between the respective divided projection data, and adding and superposing the boundary portions between the adjoining divided projection data.

Further, the projection data at an arbitrary heartbeat time phase may be formed by transferring the starting projection angle of the divided projection data, a plurality of cardiac tomograms at heartbeat time phases at with arbitrary time interval may be formed by forming a plurality of projection data including the divided projection data having different distances of starting projection angle by an arbitrary projection angle, and image-reconstructing the respective data. Further, the step of forming a plurality of cardiac tomograms at heartbeat time phases with an arbitrary time interval includes a step of performing weighing processing in the slicing direction of the object on a plurality of projection data obtained from the divided projection data necessary for image reconstruction, a step of image-reconstructing each of the plurality of projection data which has been subjected to the weighing processing and obtaining a plurality of cardiac tomograms at different slicing positions, and a step of performing interpolation or extrapolation processing to obtain a cardiac tomogram at an arbitrary slicing position from the plurality of cardiac tomograms. Further, the step of forming a plurality of cardiac tomograms at an arbitrary heartbeat time phase with an arbitrary time interval includes a step of performing interpolation or extrapolation in the slicing direction on the plurality of projection data necessary for image reconstruction obtained from the divided projection data and acquiring arbitrary projection data, and a step image-reconstructing the arbitrary projection data and obtaining a cardiac tomogram at an arbitrary slicing position. By reconstructing the cardiac tomogram using the projection data formed in the above described manner, the number of the divided projection data and the data width can be properly adjusted even when difference between phases of the heartbeat cycle of the object and the scan cycle of the helical scans is generated, whereby a cardiac tomogram having few motion artifacts can be obtained.

In the step of forming the continuous projection data, projection data at an arbitrary slicing position are formed from the collected divided projection data at the identical heartbeat time phase, and a moving image of cardiac section can be obtained by forming a cardiac tomogram from those projection data. Further, in the step of forming the continuous projection data, a plurality of projection data gathering at each heartbeat time phase in the slicing direction of the object are formed from the cardiac tomogram at arbitrary heartbeat time phases, three-dimensional cardiac images are obtained from those projection data, and thus a three-dimensional cardiac moving image can be obtained by sequentially displaying those three-dimensional images in order of the heartbeat time phase. Further, in the cardiac tomograph using an X-ray CT apparatus according to the present invention, helical scans are performed by the X-ray CT apparatus having a multi-slice X-ray detector in the slicing direction of the object and a cardiac tomogram is created by using projection data detected by the X-ray detector, including: electrocardiographic information measuring means for measuring electrocardiographic information of the object; means for finding the division number of projection data necessary for image reconstruction of a tomogram in each scan of the helical scans; projection data forming means for collecting the divided projection data in an identical heartbeat time phase on the basis of the division number of the projection data and an electrocardiographic cycle measured by the electrocardiographic information measuring means and forming projection data necessary for reconstruction of tomogram; continuous projection data forming means for forming continuous projection data by interpolating a discontinuous portion of the above formed projection data in the slicing direction of the object; image creating means for creating a cardiac tomogram of the object using the continuous projection data, and display means for displaying the above formed tomogram. The means for finding the division number of the projection data includes means for finding the scan number at which the scan cycle of the helical scan is synchronized with the electrocardiographic cycle of the object obtained by the electrocardiographic information measuring means and calculating the division number of the projection data necessary for reconstruction of a tomogram in each scan of the synchronizing scans. The continuous projection data forming means includes interpolating means for interpolating the discontinuous portion of the projection data in the slicing direction of the object with projection data in 180-degree opposite relation and in the identical heartbeat time phase, or interpolating means for interpolating the discontinuous portion of the projection data in the slicing direction of the object with interpolation using projection data in the same heartbeat time phase in the vicinity of the discontinuous portion.

The projection data used for the interpolation is obtained by weighing the projection data in the vicinity of the discontinuous portion at the same heartbeat time phase.

With the above construction, the discontinuity of the projection data in helical scans can be solved, whereby a cardiac tomogram with few motion artifacts caused by heartbeat and good image quality can be obtained.

Further, the continuous projection data forming means includes means for finding data width of the divided projection data and forms projection data at an arbitrary heartbeat time phase and in the range of projection angle necessary for image reconstruction by adjusting at least any of the starting projection angle of the divided projection data, the divided projection data number, and the data width. The projection data in the range of projection angle necessary for image reconstruction is formed by setting widely the data width of divided projection data to be wide, performing weighing processing on the data close to boundaries of the respective divided projection data, and adding and superposing the boundary portions of adjoining divided projection data. Further, the projection data at an arbitrary heartbeat time phase also can formed by shifting the starting projection angle of the divided projection data, or a plurality of projection data including the divided projection data having different distances of starting projection angle by an arbitrary projection angle are formed and a plurality of cardiac tomograms at heartbeat time phases with the arbitrary time interval can be created by reconstructing the plurality of projection data. The means for creating a plurality of cardiac tomograms at heartbeat time phases with the arbitrary time interval includes means for performing weighing processing in the slicing direction of the object on the plurality of projection data necessary for image reconstruction found from the divided projection data, means for image-reconstructing the respective projection data which have been subjected to the weighting processing to obtain a plurality of cardiac tomograms at different slicing positions, and means for obtaining a cardiac tomogram at the arbitrary slicing position by performing interpolation or extrapolation on the plurality of cardiac tomograms, and further including means for obtaining arbitrary projection data by performing interpolation or extrapolation in the slicing direction on the plurality of projection data necessary for image reconstruction found from the divided projection data, and means for obtaining a cardiac tomogram at an arbitrary slicing position by image-reconstructing the arbitrary projection data.

By reconstructing the cardiac tomograms by using thus formed projection data, the divided projection data number and the data width can be properly adjusted even when difference is generated between the phase of the heartbeat cycle of the object and that of the scan cycle of helical scans, whereby a cardiac tomogram with few motion artifacts can be obtained.

In the continuous projection data forming means, a moving image of cardiac section can be obtained by forming projection data at arbitrary slicing positions from the collected divided projection data in the identical heartbeat time phase and producing cardiac tomograms from those projection data.

Further, it is also possible to form a plurality of projection data gathering in the slicing direction of the object at each of heartbeat time phases from the obtained cardiac tomograms at arbitrary heartbeat time phases, and obtain and display three-dimensional cardiac images from those projection data, or to display a three-dimensional cardiac moving image by displaying the above three-dimensional cardiac images in order of the heartbeat time phase.

BRIEF DESCRIPTION OF THE DRAWINGS

FIG. 5 is a flow chart of the present invention.

FIG. 7 is a diagram illustrating the retrospective ECG gating.

FIG. 14 is a diagram showing another example of divided projection data collection of a projection data forming device according to the invention.

BEST MODE FOR CARRYING OUT THE INVENTION

Preferable embodiments of the present invention will be hereinafter described with reference to the accompanying drawings.

<<System Configuration>>

Figure 1:
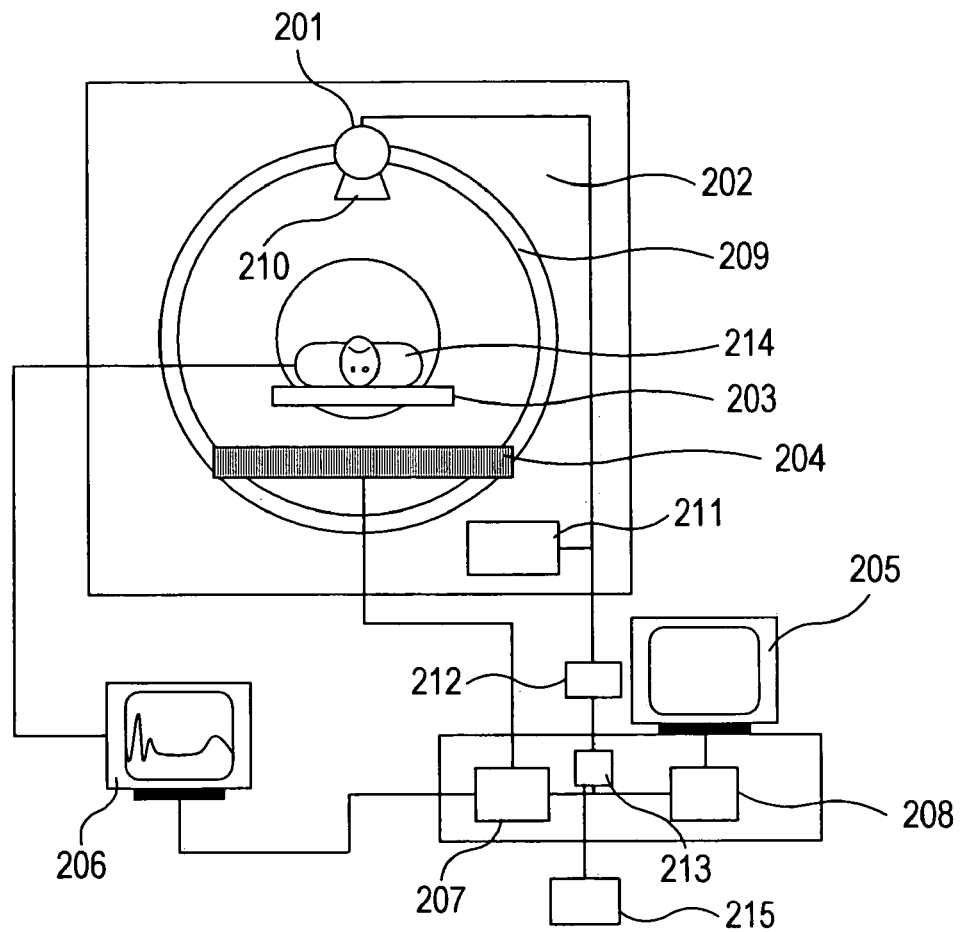
FIG. 1 is a diagram showing system configuration of an X-ray CT apparatus having a cardiac retrospective ECG gating imaging function according to the present invention.

FIG. 1 shows system configuration of an X-ray CT apparatus having a cardiac ECG gating function according to the invention. A method of producing a cardiac tomogram and tomograph using the X-ray CT apparatus according to the invention includes the scanner gantry unit 202 for radiating and detecting X-rays, the projection data forming device 207 for forming projection data from measured data detected by the scanner gantry unit 202, the image processing device 208 for processing the above formed projection data into CT image signals, and the display device 205 for outputting an CT image.

The scanner gantry unit 202 includes the rotative circular plate 209, the X-ray tube 201 mounted on the rotative circular plate 209, the collimator 210 attached to the X-ray tube 201 for controlling a direction of an X-ray bundle, and the X-ray detector 204 mounted on the rotative circular plate 209 opposite to the X-ray tube with respect to the object 214 to be examined for detecting intensities of X-rays which have passed through the object 214. The X-ray detector 204 is a multi-slice detector which can simultaneously acquire projection data at a plurality of positions by means of detector elements arranged in plural lines in the longitudinal direction of the object. Further, the rotative circular plate 209 is driven to rotate by the rotation driving device 211, which is controlled by the measurement control device 212. Further, X-ray intensity generated by the X-ray tube 201 is controlled by the measurement control means 212, which is operated and controlled by the computer 213 in accordance with scan conditions input from the input means 215. Further, the projection data forming means 207 is connected to the electrocardiograph 206 so as to acquire an electrocardiographic waveform of the object 214.

In the method of producing a cardiac tomogram and tomograph using the X-ray CT apparatus having the above-described schematic structure according to the invention, X-rays are radiated from the X-ray tube 201 while the object is laid on the table 203. A direction of those X-rays is determined by the collimator 210 and the X-rays are detected by the X-ray detector 204. At this point, the direction of X-ray radiation is changed while scanning by rotating the rotative circular plate 209 around the patient, and the X-rays are detected by the X-ray detector 204. Thus-detected measured data and the electrocardiographic information of the object 214 measured by the electrocardiograph 206 are transferred to the projection data forming device 207, projection data are formed by using the cardiac ECG gating imaging method and reconstructed into a CT image by the image processing device 208, and thus-reconstructed cardiac tomogram is displayed on the display device 205.

Figure 2:
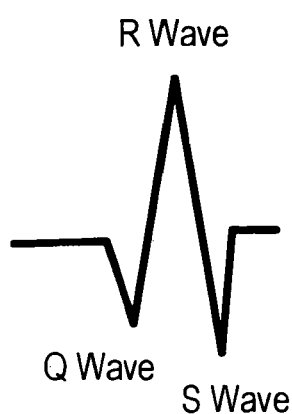
FIG. 2 is a diagram illustrating an electrocardiographic waveform.

FIG. 2 shows waveform names used in the description of the following embodiments. In the electrocardiogram, a waveform having highest value is referred to as an R wave, and waveforms before and after the R wave are respectively referred to as a Q wave and an S wave. The details can be referred to a specialized book on medical science. The present invention is aimed for creating a cardiac tomogram by applying the retrospective ECG gating to an X-ray CT apparatus constructed as shown in FIG. 1, i.e., an X-ray CT apparatus which detects projection data with a multi-slice detector by performing helical scans. However, the principle of the retrospective ECG gating imaging method being the base of the invention will be described here for the case where normal scans are performed by an X-ray CT apparatus having a single-slice detector.

Figure 3:
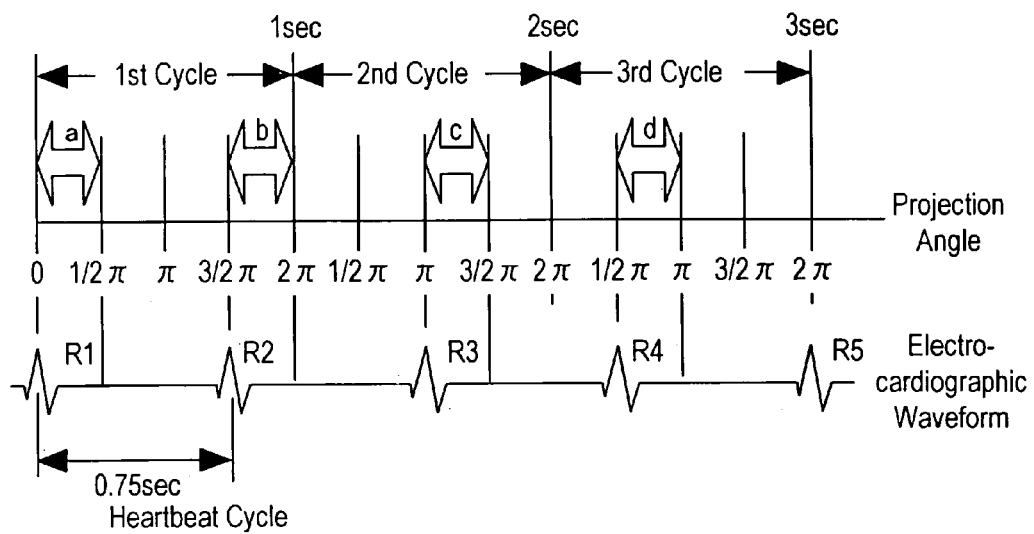
FIG. 3 is a diagram illustrating the retrospective ECG gating.

FIG. 3 is a diagram illustrating the retrospective ECG gating imaging method with a one-line X-ray detector, where the table 203 on which the object is laid in scanning remains stationary. As shown in FIG. 3, when the scan cycle is one second and the object's heartbeat cycle (R—R time) is 0.75 seconds, the scanning time phase coincides with the heartbeat time phase after three scans (i.e., after four heartbeats). Because the heart repeats four heartbeats in three scan cycles, the projection data at an identical heartbeat time phase appear four times in three scans. In the retrospective ECG gating, data at the same heartbeat time phase and at different projection angles are collected for one scan cycle. Here, since projection data for one scan cycle are collected during four heartbeat cycle, the projection angle of projection data collected during one heartbeat cycle can be expressed as $\pi/2$.

Figure 4A:
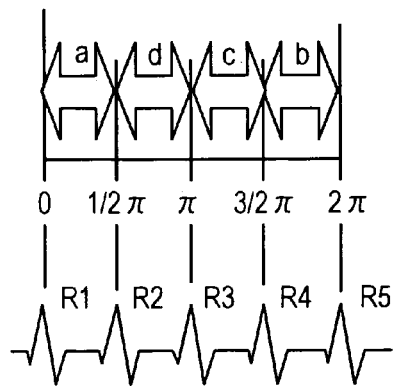
FIG. 4 is a diagram illustrating the retrospective ECG gating.
Figure 4B:
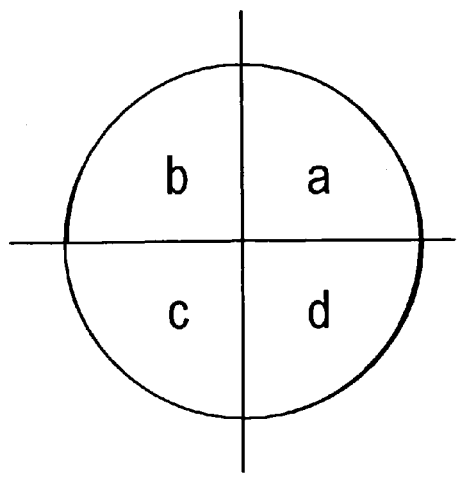

That is, in the first cycle the electrocardiographic waveforms R1 and R2 are generated, in the second cycle the electrocardiographic waveform R3 is generated, and in the third cycle the electrocardiographic waveforms R4 and R5 are generated. The heart is nearly stationary when expanding, where the electrocardiographic waveforms R1 to R5 are generated. Each of the time points of this waveform generation are regarded as a starting point, and projection data are produced at projection angles in increments of $\pi/2$. By adjoining thus obtained data in order of projection angle, the projection data for one stationary cardiac image can be obtained. The reference characters a, b, c, and d in FIG. 3 represents partial projection data when imaging is performed at projection angles in increments of $\pi/2$ from the starting points R1, R2, R3, and R4, respectively. By executing the imaging, the projection data shown in FIG. 4(a) are produced. Those data are collected after R wave is generated during each heartbeat cycle in increments of $\pi/2$, having respectively different projection angles. That is, it is equivalent to that scans are performed over 360 degrees during the time in which scans are performed at the projection angle $\pi/2$. As shown in FIG. 4(b), the data in the portions a and b are collected during the first scan cycle, those in the portion d are collected during the third scan cycle, and those in the portion C are collected during the second scan cycle. That is, one unit of projection data shown in FIG. 4(a) is formed by aligning the partial projection data a, b, c, and d shown in FIG. 3 in order of projection angle 0 to $2\pi$. Accordingly, the partial projection data a, b, c, and d are aligned in order of the electrocardiographic waveforms R1, R4, R3, R2, and R5. FIG. 4(b) shows an example of projection data for one cardiac image constructed by collecting the partial projection data a, b, c, and d. In the figure, the partial projection data a correspond to first $\pi/2$, i.e. the range 0 to $\pi/2$, the partial projection data d correspond to $\pi/2$ to $\pi$, and the partial projection data c and d respectively correspond to $\pi$ to $3\pi/2$ and $3\pi/2$ to $2\pi$. The projection data for one image is thus produced.

According to this retrospective ECG gating (example in FIG. 3), scans are performed for 360 degrees within the time in which the scans are performed for projection angle $\pi/2$. Therefore, the theoretical scan time is 0.25 second, whereby cardiac imaging can be performed at high speed with the current three-generation CT in which one scan takes one minute. Further, more rapid scan also can be performed depending on the scan time and heartbeat time.

FIG. 5 shows a brief flow of cardiac imaging. First, in Step 1 a scan cycle needed in step 3 is found on the basis of scan time and a heart rate of the object. That is, in Step 1, the scan number=3 as the necessary scan number at which scan is synchronized with heartbeat and the projection data division number=¼[FIG. 4(a), (b)] are determined from one second of scan time and 0.75 seconds of object's heart rate shown in FIG. 3. In Step 2 imaging is performed on the basis of the scan number found in Step 1.

In Step 3, the projection data forming device 207 collects projection data (a to d in FIG. 3) in a matching heartbeat time phase from various scan cycles on the basis of electrocardiographic information (R1 to R5 in FIG. 3) obtained from the object 214. In FIG. 4, the projection data obtained in Step 3 is reconstructed into an image by the image processing device 208. This image is a tomogram showing heart which appears to be stationary.

<<Response to Discontinuity of Projection Data>>

A method of producing a cardiac tomogram and tomograph using an X-ray CT apparatus according to the first embodiment of the present invention will be described, in which a cardiac tomogram having few artifacts caused by discontinuity of projection data can be obtained when the retrospective ECG gating imaging method is applied to helical scan in which the table moves.

(1) In the Case Where the Discontinuous Portion of Projection Data is Narrow

Figure 6:
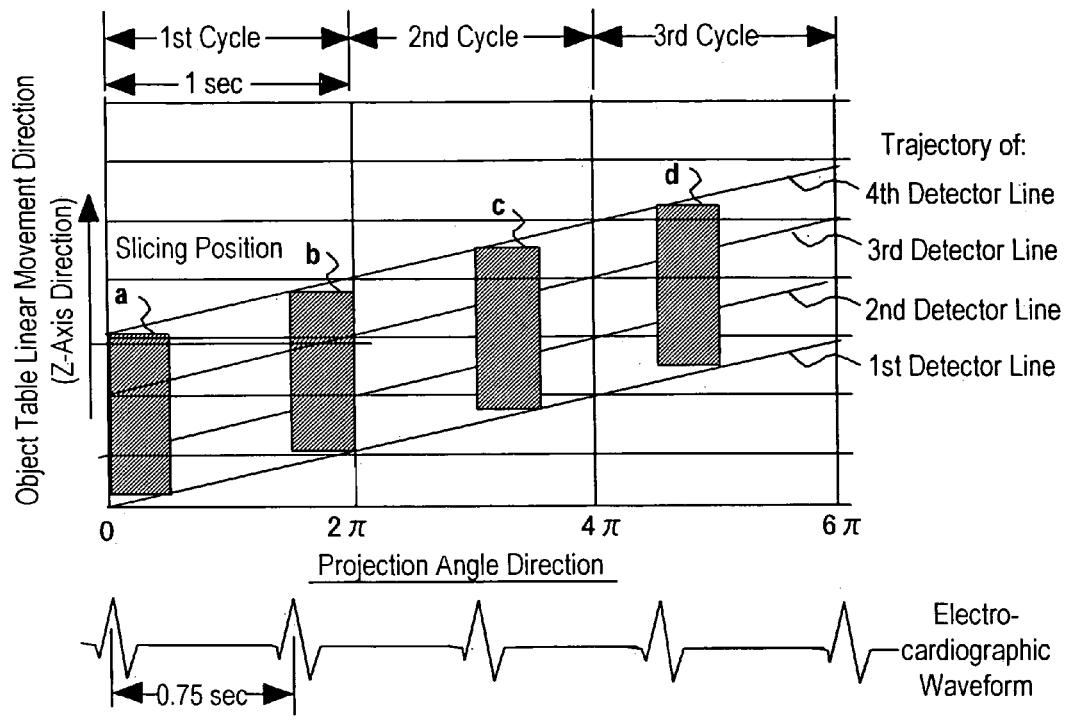
FIG. 6 is a diagram illustrating the retrospective ECG gating in helical scans in the case where multiple X-ray detector lines are used.

FIG. 6 shows a case where the multi-slice detector having four lines is used, a scan cycle is 1 second, a heartbeat cycle is 0.75 seconds, and the discontinuous portion of projection data is narrow.

In the figure, the ordinate axis designates a linear movement direction of a table on which the object to be examined is laid (longitudinal direction of the object, also referred to as Z-axis direction), and the abscissa axis designates a projection angle. Trajectory of the detector traces the center of each detector. The helical scan pitch is "pitch 1" in which the table moves for one detector as one scan is finished. That is, when a third scan is finished, the position of the first detector line is the same as the fourth detector line at a first scan (when the projection angle is zero). In FIG. 6, because it is hypothesized that the table is fixed and the X-ray source and the X-ray detector are moved (actually, the X-ray source and the X-ray detector are not moved and the table is transferred), the trajectory of the X-ray detector can be described as a straight line having inclination.

In FIG. 6, shaded areas correspond to projection data at the same heartbeat time phase collected as in FIG. 3.

Since there are four heartbeat cycles in three scan cycles in the case of FIG. 6 too, projection data for one scan can be obtained by collecting projection data for $\pi/2$. In the case of FIG. 6, because four-line detector is used, the projection data to be collected has a width of the detector, which is described by shaded rectangles. That is, within the rectangle, the projection data of an arbitrary slicing position can be calculated with interpolation between projection data obtained by an adjoining detector. That is, one scan cycle is 1 second and the projection angle is 0 to $2\pi$. This scan is performed for three cycles, and the projection data a, b, d, and d are obtained respectively at the electrocardiographic waveforms R1 to R4.

In FIG. 7, the projection data obtained in each scan cycle in FIG. 6 are shown as data for one scan by moving the rectangles in parallel within the zone of the first scan. That is, the projection data are aligned in order of a, d, c, and b within the projection angle 0 to $2\pi$. In FIG. 7, the projection data collected in each cycle are described in phase because helical scans are performed and so the collected data shift in the linear movement direction of the object table (Z-axis direction). For example, the slicing position SP shown in FIG. 7 is always within the shaded rectangles, whereby it can be calculated at any projection angle. The interpolation can be realized by using a simple linear interpolation in which weight is added in correspondence with distance as shown in FIG. 8.

Figure 8A:
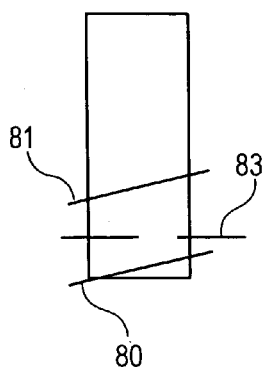
FIG. 8 is a diagram illustrating interpolation.
Figure 8B:
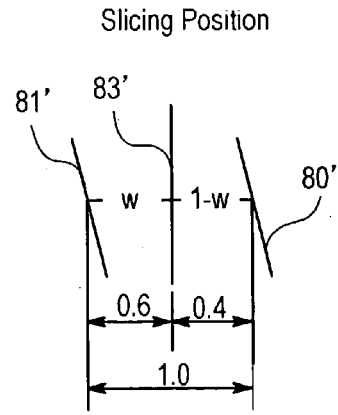

In FIG. 8, the projection data in the zone $\pi$ to $3\pi/2$ shown in FIG. 3 are extracted for the purpose of illustration. In this case, the projection data at a desired slicing position of a three-line or four-line detector are calculated. That is, FIG. 8(a) shows the case where the slicing position 83 is calculated with the third detector line 80 and the fourth detector line 81 by means of known general linear interpolation. Also, FIG. 8(b) shows an example of calculating the slicing position 83', in which a mean position between the trajectories 80' and 81' of the detector is set to be 1.0 for instance, the weight between the slicing position 83' and the trajectory 80' is set as w=0.4 and the weight between the slicing position 83' the trajectory 81' is set as w=0.6 to calculate the slicing position. The slicing position 70 shown in FIG. 7 is thus calculated.

Figure 9:
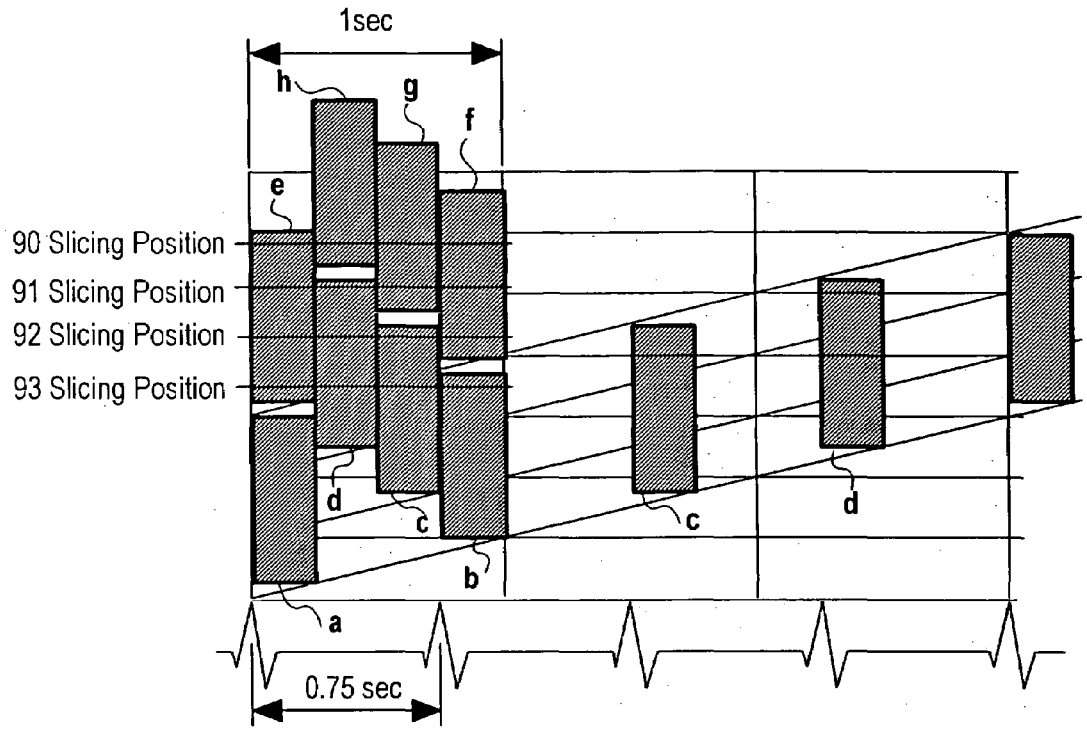
FIG. 9 is a diagram illustrating the retrospective ECG gating in helical scans in the case where multiple X-ray detector lines are used.

Although FIGS. 6 and 7 show the first to third scans, FIG. 9 further shows the projection data collected in scans which are moved in parallel within the zone of first scan. By continuously scanning, projection data having the identical heartbeat time phase and different projection angle can be calculated at various slicing position as shown in FIG. 9. That is, the projection data a, b, c, and d respectively correspond to the first to third cycles, and the projection data e, f, g, and h correspond to the fourth to sixth cycles. In this case, because each of projection data are involved with any one of the slicing positions 90 to 93, image data at an arbitrary slicing position can be produced.

(2) In the Case Where the Discontinuous Portion of Projection Data is Wide

Next, the case where heartbeat is different will be described. In the example, a scan cycle is 1 second, a heartbeat cycle is 0.8 seconds, and a helical scan pitch is 1, where the scan is synchronized with the heartbeat when the scan cycle is four and the heartbeat cycle is five. Here, the projection data are collected at projection angles in increments of $2\pi/5$. According to the present invention, a width and the like of projection data collected is determined by the projection data forming device 207.

Figure 10:
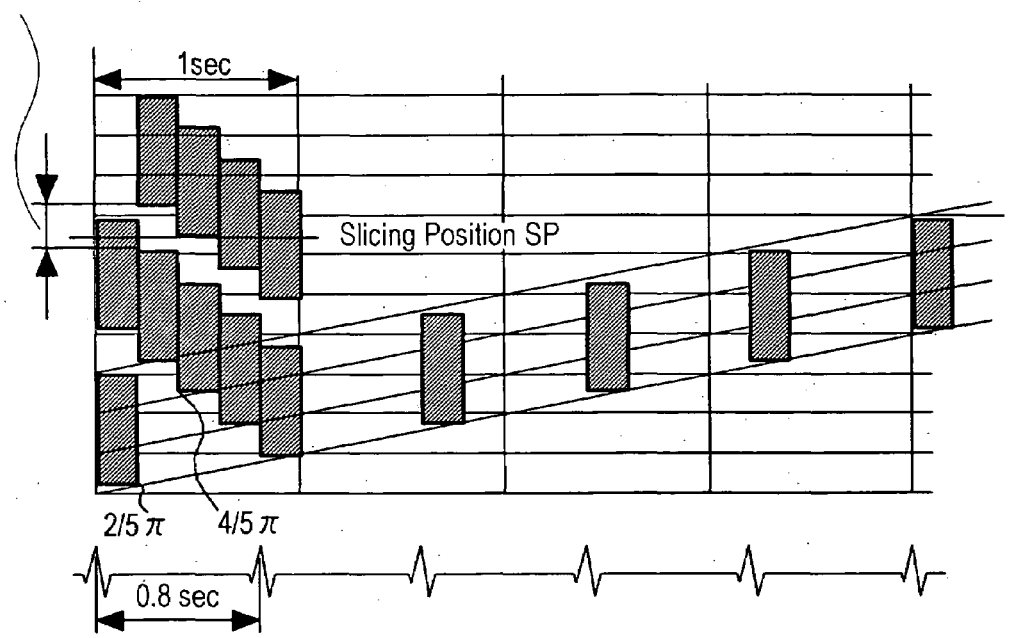
FIG. 10 is a diagram illustrating discontinuous projection data.

In the same manner as the description of FIGS. 6, 7, and 8, the above example can be illustrated as FIG. 10. When the projection data at the slicing position SP is calculated, in the zone of $2\pi/5$ to $4\pi/5$ a portion 110 is generated where projection data are discontinuous and they cannot be calculated because some of rectangles are not involved with the slicing position. Here, the projection data cannot be calculated.

Figure 11:
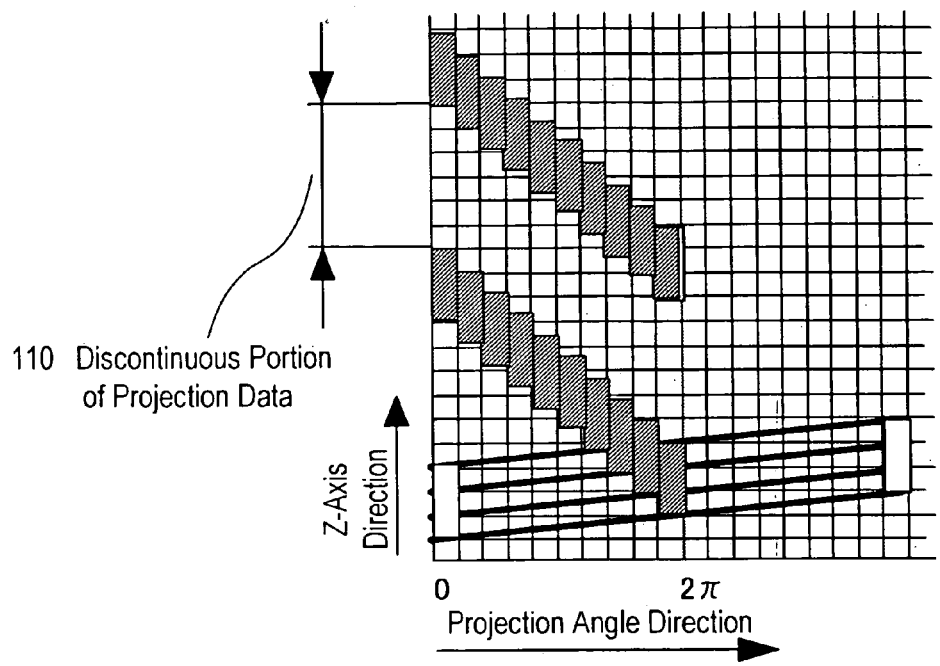
FIG. 11 is a diagram illustrating discontinuous projection data.

Although a discontinuous portion is generated in the example of FIG. 9, the zone thereof is much narrower than in the example of FIG. 10 and so the projection data can be calculated at various slicing positions. In FIG. 10, however, the number of slicing positions where projection data cannot be calculated greatly increases because the width of discontinuous zone is wide. FIG. 11 shows an extreme example, where it is hypothesized a scan cycle is 1, and a heartbeat is 0.9 seconds. In the case of FIG. 11, a width of collected projection data is $\pi/5$, and projection data for nine cycles are necessary. The projection data for one scan are collected by performing scans for as many as nine cycles. In the helical scan, because the object table is sequentially moved during nine cycles, the discontinuous portion 110 of projection data becomes greatly large as shown in FIG. 11. Accordingly, projection data at a desired slicing position cannot be calculated.

Figure 12A:
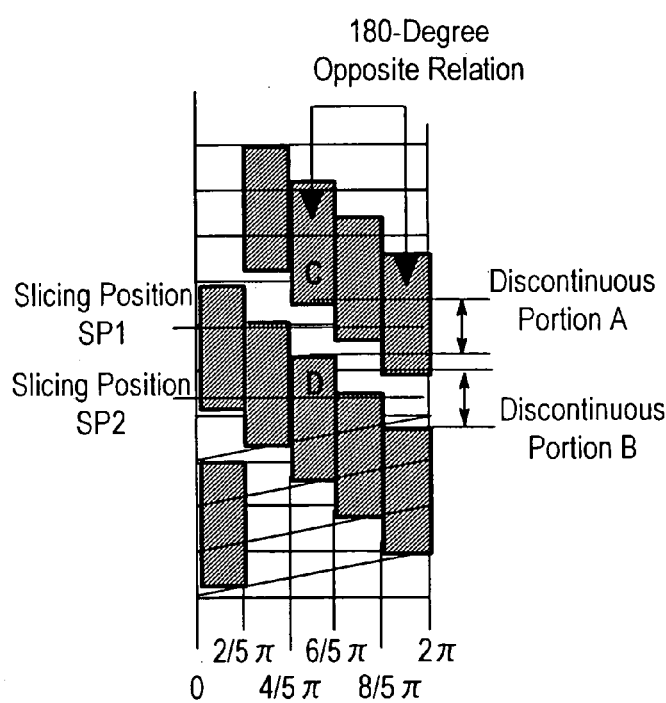
FIG. 12 is a diagram illustrating interpolation of a discontinuous portion.

According to the present invention, the above problems are solved as below. FIG. 12(a) shows the retrospective ECG gating scan in the case where one-second scan is repeatedly performed at 0.8-second heartbeat cycle. As shown in FIG. 12(a), for example, discontinuity of projection data is generated at the slicing position SP1 in the zone $4\pi/5$ to $6\pi/5$ (discontinuous portion A).

Also, at the slicing position SP2 a discontinuous portion is generated in the zone $8\pi/5$ to $2\pi$ (discontinuous portion B). Since projection data at a desired slicing position cannot be calculated with a discontinuous portion, if these data are image-reconstructed, an image obtained has artifacts or low image quality.

As shown in FIG. 12(a), the zone $4\pi/5$ to $6\pi/5$ and that $8\pi/5$ to $2\pi$ are in 180-degrees opposite relation. "Opposite relation" means that X-ray paths passing through the same zone, but the X-ray incident angles are opposite by 180 degrees. That is, 180-degree opposite data are theoretically identical in scans in which the object table is stationary.

In FIG. 12(a), the data in the opposite relation are not the same because the respective positions of the object table (slicing position) are different. However, it is a very effective correction to eliminate the discontinuous portion by replacing the discontinuous portion with projection data in the 180-degree opposite relation. That is, in the retrospective ECG gating imaging, it is supposed that projection data at an identical heartbeat time phase are collected so as to suppress cardiac motion artifacts as much as possible. Accordingly, when the discontinuous portion A shown in FIG. 12(a) is replaced with any projection data, the substitute projection data must be in the 180-degree opposite relation and at the same heartbeat time phase. Because all the shaded square portions represent data at the same heartbeat time phase, among them the projection data in the opposite relation are those in 180-degree opposite relation and at the same heartbeat time phase are used.

Figure 12B:
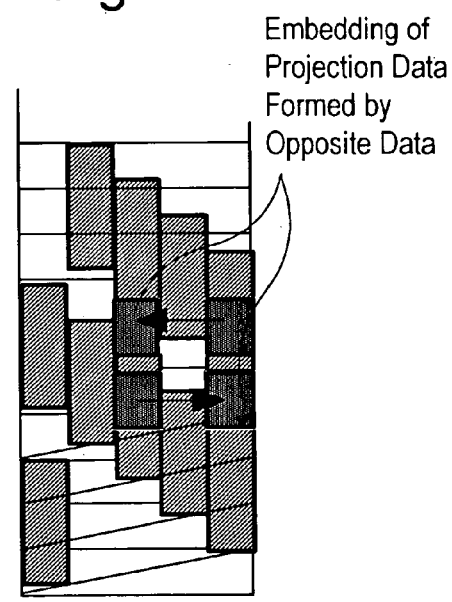

FIG. 12(b) shows an example in which projection data in the opposite relation and at the same heartbeat time phase are embedded to a discontinuous portion. In FIG. 12(b), the discontinuous portion is removed due to embedding processing and so the projection data at the slicing position SP1 can be calculated. Meanwhile, in the discontinuous portion B, the zone of $8\pi/5$ to $2\pi$ is discontinuous. It also can be solved by embedding the data of $4\pi/5$ to $6\pi/5$ in the 180-degree opposite relation, and the projection data at the slicing position SP2 can be calculated. Further, the number of divided projection data may be found by storing a table of relation between the heartbeat cycle and the divided projection data number into memory of the projection data forming device and referring to this memory.

Although the projection data in an opposite relation is used in the above example, the projection data of a discontinuous portion at slicing position SP1 also can be calculated from the shaded squares C and D. While the reliability thereof is lower than the above method using the 180-degree opposite data, it is suitable for cardiac imaging since data at the identical heartbeat time phase is used.

Meanwhile, in the above description, the method using data in the 180-degree opposite relation and at the same heartbeat time phase and the method of calculation utilizing linear interpolation using adjoining projection data are adopted. Since the data at the same heartbeat time phase are used in both cases, the obtained cardiac tomogram has few motion artifacts.

<<Optimization and Reconstruction of Phase Difference Between Heartbeat Cycle and Scan Cycle>>

Next, a method of producing a cardiac tomogram and tomograph according to the second embodiment of the present invention will be described, in which a cardiac tomogram (two-dimensional image), a three-dimensional image, and a four-dimensional image (moving image) can be obtained by optimizing projection data in correspondence with phase difference between a heartbeat cycle and a scan cycle when projection data of the continuous portion obtained by the present invention described above, i.e., projection data at a matched heartbeat time phase are collected in each scan cycle.

Meanwhile, the X-ray detector 204 used for creating a cardiac tomogram according to the invention is a multi-slice detector in which a plurality of detector elements are aligned in the longitudinal direction of an object to be examined so as to acquire projection data of a plurality of positions at once, and the scan system here is the helical scan.

As described in FIG. 1, X-rays are radiated from the X-ray tube 201 while the object 203 to be examined is laid on the object table 203. The direction of those X-rays is determined by the collimator 210, and the X-rays are detected by the X-ray detector 204. Here, X-rays are detected by the X-ray detector 204 while the direction of X-ray radiation is varied in scans by rotating the rotative circular plate 209 around the object. Thus detected measured data are transferred to the projection data forming device 207, in which projection data having few motion artifacts are formed from electrocardiographic information of the object (see FIG. 2 and related descriptions) and imaging conditions obtained from the measurement control device 212. Further, thus obtained projection data are reconstructed by the image processing device 208 into a CT image, which is output on the display device 205 as three- or four-dimensional (moving) image, the details of which will be described below.

(1) Collection of Projection Data

Figure 13A:
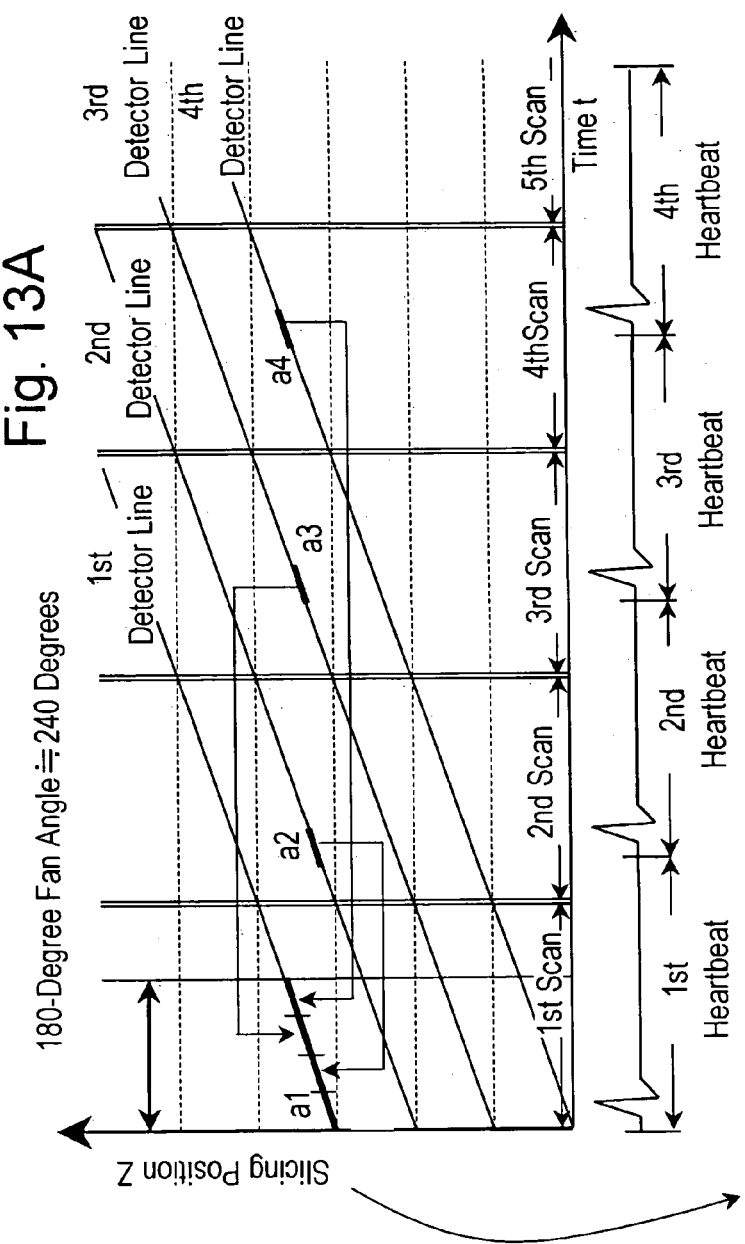
FIG. 13 is a diagram showing one example of divided projection data collection of a projection data forming device according to the invention.
Figure 13B:
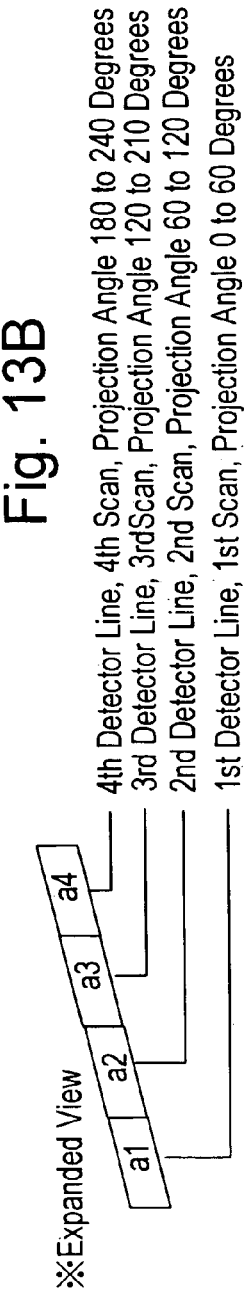

FIG. 13 shows an example where the ratio of the scan cycle and the heartbeat cycle is 6:7. Meanwhile, in FIG. 13(A), timing of divided projection data collection of the projection data forming device 207 in the X-ray CT apparatus is shown. Further, FIG. 13(B) is an expanded view of the divided projection data collection during a period of "180 degrees+fan angle≈240 degrees" which is necessary for reconstruction shown in FIG. 13(A). In FIG. 13(A), the abscissa axis indicates time (t) and the ordinate axis indicates positions in a linear movement direction (Z axis) of the object table.

Further, ECG signals from the electrocardiograph 206 are shown below the abscissa axis, where positions of heart strokes in the time direction (t) are represented. Meanwhile, imaging conditions at this point are determined on the assumption that a helical pitch is 1, a four-line detector is used, and the ratio of the scan cycle and the heartbeat cycle is 6:7. Here, the helical pitch is defined as a ratio to a detector element alignment pitch in the Z-axis direction.

Along the ordinates in FIG. 13(A), four oblique lines indicate trajectories of rotation center of four detectors when helical scan is performed. Thick lines on the center trajectories of the detector element centers indicate divided projection data at an identical heartbeat time phase described in the above embodiment. Here, the respective divided projection data are shown as a1, a2, a3, and a4. For easy understanding of the divided projection data collection method, the projection data after collection in the first scan are shown. A rectangle divided into four portions in FIG. 13(B) is an expanded view of projection data after collection, in which each of the divided portions represents the respective divided projection data. In the figure, detector data of the respective divided projection data, the scan number from scan start, and the range of projection angle are clearly stated.

In this case where the ratio of the scan cycle and the heartbeat cycle is 6:7, the divided projection data a1 obtained by the first detector line at the first scan projection angle 0 to 60 degrees, the divided projection data a2 obtained by the second detector line at the second projection angle 60 to 120 degrees, the divided projection data a3 obtained by the third detector line at the third scan projection angle 120 to 180 degrees, and the divided projection data a4 obtained by the fourth detector line at the fourth scan projection angle 180 to 240 degrees are the divided projection data in the same range of ECG signals. It is clear that the projection data at a projection angle (approximately 240 degrees) being the sum of 180 degrees necessary for image reconstruction and a fan angle of the X-ray source are successfully collected from four divided projection data having the same data width.

By image-reconstructing the projection data collected by using the above algorithm, time resolution becomes one-sixth of scan time and a reconstructed image with few motion artifacts can be obtained. Meanwhile, because the above imaging conditions in FIG. 13 fundamentally enable to form projection data with few motion artifacts, they are regarded as ideal conditions here.

However, the conditions in which the projection data collection method described in FIG. 13 can be applied only in the case where the ratio of a scan cycle and a heartbeat cycle is 6:7. If the projection data collection method of FIG.

13 is applied under the conditions of other ratio, divided projection data at an identical heartbeat time phase cannot be collected, and so an image with few motion artifacts cannot be reconstructed.

To solve the above problem, for example, it is possible to bring the imaging conditions close to ideal ones by mechanically changing scan time. However, because there is a limit on the range of scan time to be finely adjusted with mechanical change, divided projection data at the identical heartbeat time phase cannot be collected and so it is impossible to obtain a reconstructed image with few motion artifacts.

Therefore, according to the present invention, a projection data collection method is proposed by which a reconstructed image with few motion artifacts can be obtained by adjusting the number and width of divided projection data in accordance with the object's heartbeat cycle.

First, the calculation method of a division number of divided projection data and a divided projection data width will be mentioned. Supposing that a divided projection data width is Sv (view), scan time is St(s), one heartbeat cycle is Cc(s), an imaging view number is Vw(view), collected divided projection data number is Sn, a view number necessary for reconstruction is Hv, and a detector line number is Dn, the divided projection data width Sv and the collected divided projection data number Sn can be calculated with the following formulas (1) and (2):

$$Sv = |St - Cc| \times (Vw/St) \quad (1)$$

$$Sn = Hv/Sv \text{ (rounded to a nearest integer number)} \quad (2)$$

Hereinafter, the details will be described with reference to various examples.

FIG. 14 shows the case where the ratio of scan cycle and heartbeat cycle is 36:43.

Contents shown in FIG. 14 are similar to FIG. 13. However, the imaging conditions are determined as that a helical pitch is 1, four-line detector is used, and the ratio of scan cycle and heartbeat cycle is 36:43.

In comparison with the above-described ideal conditions, the ratio here is set for the case where the heartbeat cycle is longer than the scan time by the time necessary for the X-ray source 201 to move by 10 degrees. Divided projection data to be collected are respectively described as b1, b2, b3, and b4.

When the ratio of scan cycle and heartbeat cycle is 36:43, projection data for a projection angle (approximately 240 degrees) being the sum of 180 degrees necessary for image reconstruction and a fan angle of the X-ray source are collected by combining the divided data b1 at the projection angle 0 to 70 degrees obtained by the first detector line, the divided projection data b2 at the projection angle 70 to 140 degrees obtained by the second detector line, the divided projection data b3 at the projection angle 140 to 210 degrees obtained by the third detector line, and the divided projection data b4 at the projection angle 210 to 240 degrees obtained by the fourth detector line (see the expanded view of FIG. 14(B)).

In the divided projection data collection method shown in FIG. 14, in comparison with the method of FIG. 13, the data width of the divided projection data b1, b2, and b3 are respectively increased by 10 degrees, while that of b4 is decreased by 30 degrees, which is the sum of added angles of the data width of b1, b2, and b3, to be 30 degrees. Furthermore, the divided projection data starting angle of b2, b3, b4 are increase respectively by 10 degrees, 20 degrees, and 30 degrees, whereby the divided projection data b1, b2, b3, and b4 have the identical heartbeat time phase (see ECG signals shown at the bottom of FIG. 14(A)).

As shown in FIG. 14, by image-reconstructing the projection data collected by using the divided projection data collecting method in which the data width of divided projection data is adjusted, time resolution becomes seven-thirty-sixth of the scan time and a reconstructed image with few motion artifacts can be obtained.

FIG. 14 shows the divided projection data collecting method in the case where the ratio of scan time and heartbeat cycle is 36:43 (the case where the heartbeat cycle is longer than the scan time by the time necessary for the X-ray source to move by 10 degrees in comparison with the ideal conditions). Further, even when difference between the scan time and the heartbeat cycle is large, projection data at an identical heartbeat time phase can be obtained similarly by changing the number of divided projection data collected and the data width thereof.

Figure 15:
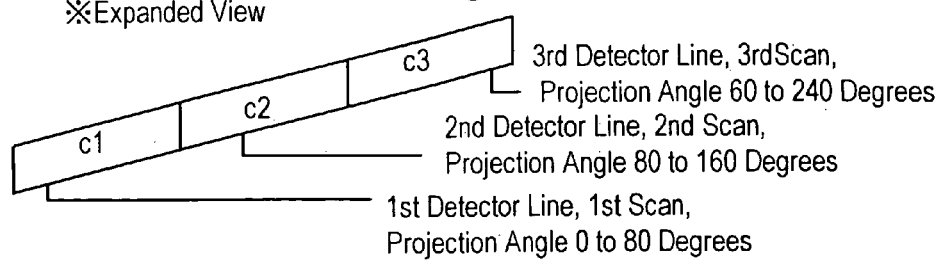
FIG. 15 is a diagram showing still another example of divided projection data collection of a projection data forming device according to the invention.

FIG. 15 shows the divided projection data collecting method in the case where the ratio of scan time and heartbeat cycle is 18:23 (the case where the heartbeat cycle is longer than the scan time by the time necessary for X-ray source to move by 20 degrees, projection data in comparison with the ideal conditions). Meanwhile, only an expanded view is shown here in order to avoid duplication of description, wherein the divided projection c1, c2, and c3 are shown. By increasing the data width of those projection data c1, c2, and c3 respectively by 20 degrees and decreasing the number of the divided projection data to be collected to three, projection data with few motion artifacts can be obtained as in the above method.

By image-reconstructing the projection data collected by using the divided projection data collection method for adjusting data width of the divided projection data shown in FIG. 15, time resolution becomes two-ninth of scan time and a reconstructed image with few motion artifacts can be obtained.

Further, even in a case where the ratio of scan cycle and heartbeat cycle does not coincide with any of the cases described in FIG. 13 to 15, a reconstructed image with few motion artifacts can be produced in the similar manner by adjusting the width and the number of divided projection data in accordance with the heartbeat cycle of the object and collecting divided projection data at an identical heartbeat time phase.

However, if the imaging condition is greatly different from the ideal conditions (i.e., the ratio of scan cycle heartbeat cycle is 6:7), the number of divided projection data is reduced and the width of divided projection data becomes large, and so motion artifacts of the obtained reconstructed image increases. Accordingly, to obtain a reconstructed image with fewer motion artifacts, it is desirable to preset the scan time in measurement to be close to that in the ideal conditions before utilizing the invention.

Further, when the divided projection data is collected, a heartbeat time phase rapidly changes in the boundary portion and so motion artifacts are generated when a cardiac tomogram is created. To solve this phenomenon, it is contemplated to set widths of the respective divided projection data to be wider, perform weighing processing on data of the boundary portion of the divided projection data, and add up and superpose the boundary portions of the adjoining divided projection data.

Further, even when a patient's heart stroke becomes irregular due to arrhythmia, the present invention can be utilized by adjusting data width of divided projection data and the collected data number using information of heart strokes (i.e., ECG signal described above) obtained from the electrocardiograph.

(2) Image Reconstruction

Figure 16:
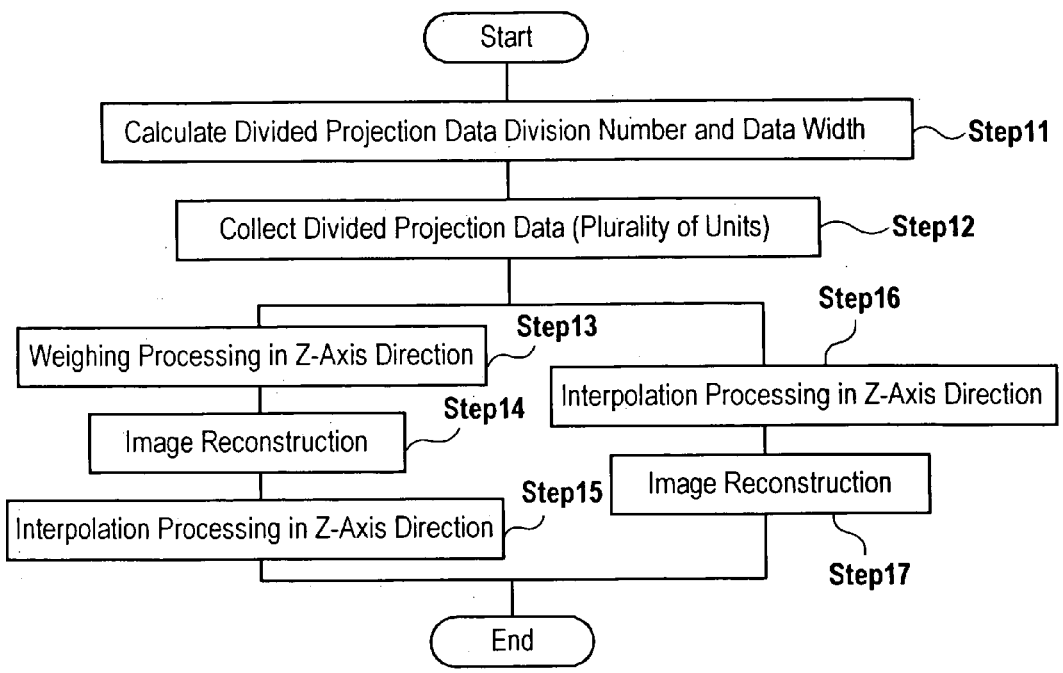
FIG. 16 is a flow chart of processing performed by the projection data forming device and an image processing device according to the invention.

Next, the above-obtained image reconstruction after producing projection data will be described with reference to FIGS. 16, 17, 18, and 19. It is necessary to perform some processings on the produced projection data to obtain a cardiac tomogram at an arbitrary slicing position. First, FIG. 16 shows the flow of obtaining a cardiac tomogram. An object's heart rate, a division number of divided projection data, and a data width are found from imaging conditions as described above (step 11), and the projection data are produced by collecting divided projection data (step 12). Meanwhile, FIGS. 13, 14, and 15 described above show the methods of collecting one unit of projection data. However, in practice, it is also possible to collect a plurality of units of projection data of various slicing positions.

Accordingly, production of the plural units of projection data will be described with reference to FIG. 17.

Figure 17:
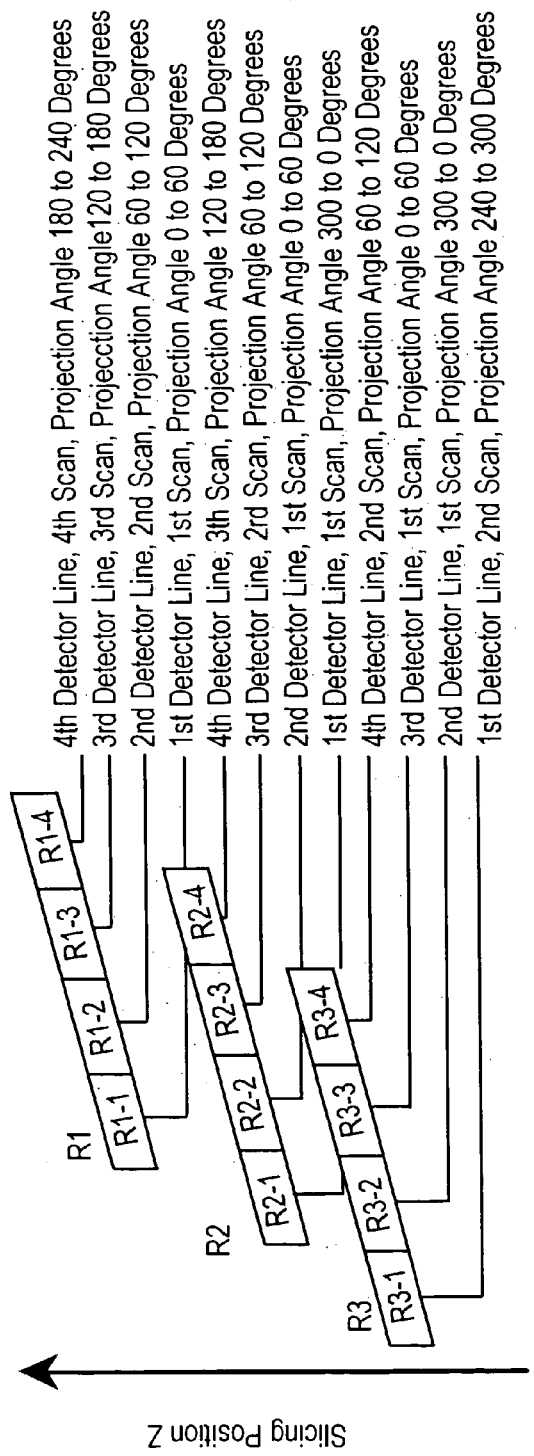
FIG. 17 is a diagram illustrating the details of the processing shown in FIG. 16.

First, FIG. 17 shows an example of producing projection data under the ideal conditions illustrated in FIG. 13. Three units of projection data in different slicing ranges are produced from data of four detector lines. The projection data obtained are shown as R1, R2, and R3, and the detector data used, the scan number from scan start, and the projection angle range are shown with regard to the respective divided projection data collected. A first scan is regarded as the basis, and previous scans are shown as minus.

Two methods of obtaining a cardiac tomogram at a certain slicing position from these three units of projection data will be described.

Figure 18:
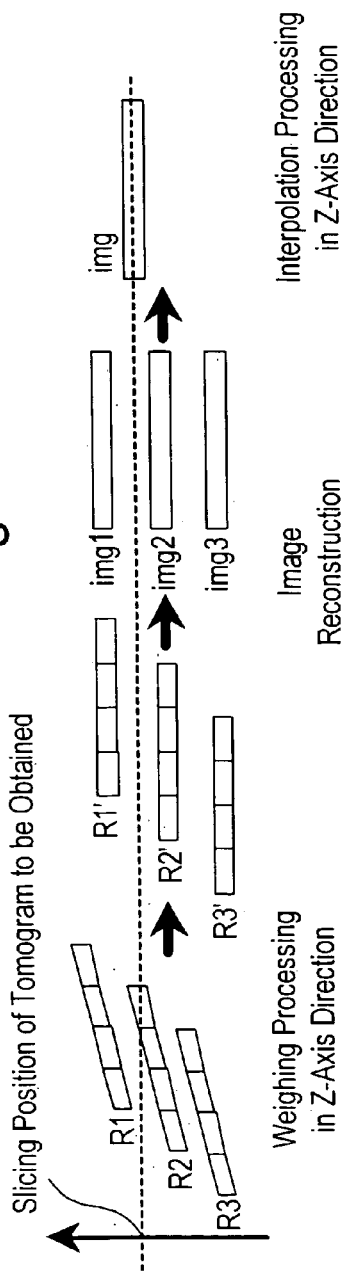
FIG. 18 is a diagram illustrating the details of the processing shown in FIG. 16.

The first method will be described with reference to FIG. 16 and FIG. 18. The ordinate axis in FIG. 18 indicates positions in the slicing direction, and a cardiac tomogram at a slicing position shown by a broken line is obtained. Therefore, first, weighing processing in the Z-axis direction is performed on the three units of projection data R1, R2, and R3 (Step 13 in FIG. 16), and thus the projection data at a certain slicing position are produced. Next, the projection data R1', R2', and R3' after the processing are image-reconstructed (Step 14) to obtain three cardiac tomograms at different slicing positions. Interpolation or extrapolation processing (Z-axis direction interpolation/extrapolation processing) are performed on the basis of finally obtained three cardiac tomograms img1, img2, and img3 (Step 15), and thus a cardiac tomogram img at an arbitrary slicing position can be obtained.

Figure 19:
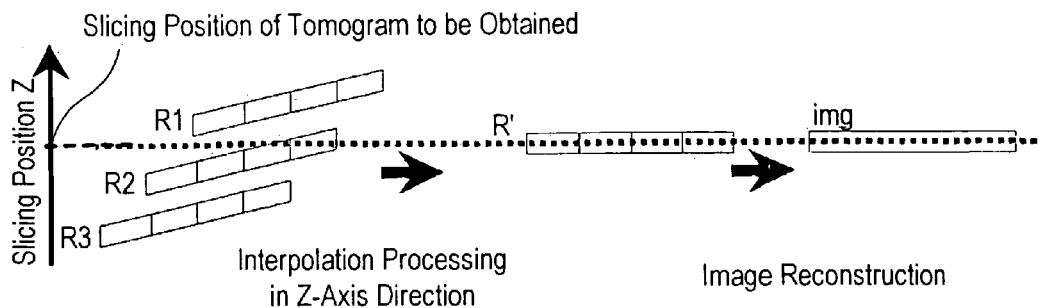
FIG. 19 is a diagram illustrating the details of the processing shown in FIG. 16.

Next, the second method will be described with reference to FIG. 19. In this method, interpolation or extrapolation in the slicing direction is performed on the basis of three units of produced projection data R1, R2, and R3, and projection data R' at an arbitrary slicing position is thus obtained (Z-axis direction interpolation/extrapolation processing) (Step 16 in FIG. 16). Then, image reconstruction is performed on the projection data R' (Step 17) to obtain a cardiac tomogram img at arbitrary slicing position.

Figure 20:
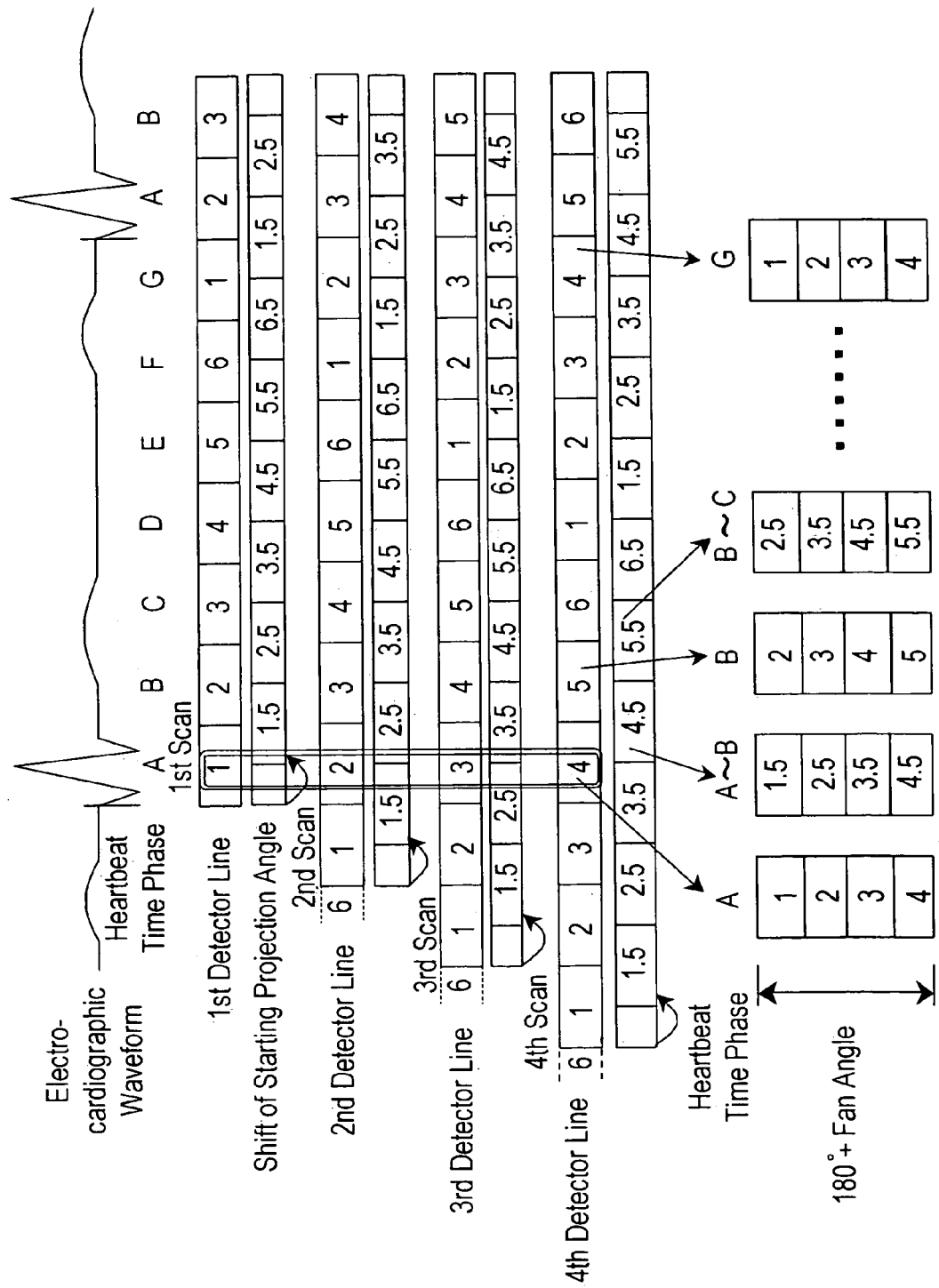
FIG. 20 is a diagram showing one example of collection of divided projection data at an arbitrary heartbeat time phase performed by the projection data forming device according to the invention.

Furthermore, referring to FIG. 20, a method of forming projection data in a projection angle range necessary for image reconstruction in an arbitrary heartbeat time phase instructed by an operator will be described. FIG. 20 shows a method of collecting divided projection data at the respective heartbeat time phases under the same conditions as in FIG. 13. That is, the imaging conditions are determined on the assumption that a helical pitch is 1, four-line detector is used, and the ratio of the scan cycle and the heartbeat cycle is 6:7. As described above, under the ideal conditions, a reconstructed image with few motion artifacts can be obtained by using four units of divided projection data having an identical heartbeat time phase and an identical data width.

In the figure, an electrocardiographic waveform (ECG signal) is shown in the upper part. Under that, the heartbeat time phases in the case where one heartbeat is divided into seven heartbeat time phases are shown with reference characters A to G respectively. Then, projection data obtained by four detectors are respectively shown with zonal rectangles, in which one scan is divided by projection angle widths of divided projection data, which is shown with reference numbers 1 to 6 in ascending order of projection angle. Further, for easy understanding of the divided projection data collection method, the projection data obtained by the second detector line, those obtained by the third detector line, and those obtained by the fourth detector line are collected respectively from the second scan, third scan, and fourth scan in the figure.

Further, since the ratio of the scan cycle and the heartbeat cycle is 6:7 in the figure, as the scan proceeds the heartbeat time phases of divided projection data 1 to 6 obtained by the respective detectors shift by one heartbeat time phase. At the bottom of the figure, projection data after the divided projection data collection are shown. For example, when the projection data in the heartbeat time phase A are formed, the projection data necessary for image reconstruction can be obtained by collecting four divided projection data (portion enclosed by double lines). Further, examples of forming projection data in the heartbeat time phases B and G are also shown in the figure.

Next, as an example of forming projection data at an arbitrary heartbeat time phase, projection data in a heartbeat time phase in the middle of the heartbeat time phase A and the heartbeat time phase B are assumed to be obtained. In this case, first, a starting projection angle of divided projection data of the projection data obtained by each detector is shifted in a moving direction of the X-ray source by a half angle of the projection angle of divided projection data (30 degree). Projection data after changing the starting projection angle at each detector are shown below the projection data line before the change, in which the respective projection data are set to be 1.5, 2.5, . . . and 6.5.

Also in this case, as in the above case of forming projection data in the heartbeat time phase A, projection data at a heartbeat time phase in the middle of the heartbeat time phase A and the heartbeat time phase B by collecting divided projection data after shifting the starting projection angle of divided projection data. The collected projection data in the heartbeat time phase A–B are shown at the bottom of FIG. 20. In a similar collection method, projection data in the middle of two heartbeat time phases, such as the heartbeat time phase B and the heartbeat time phase C, can be obtained.

Thus, a method of collecting projection data in a heartbeat time phase in the middle of the respective heartbeat time phases by shifting the starting projection angle of divided projection data has been described. According to that, by changing a distance of the starting projection angle of divided projection data, projection data at an arbitrary heartbeat time phase can be formed.

Further, it is also possible to create a plurality of cardiac tomograms in a heartbeat time phase with an arbitrary time interval by forming a plurality of projection data units having different distance of starting projection angle by an arbitrary projection angle and image-reconstructing them.

(3) Creation of Three-Dimensional Image and Four-Dimensional Image (Moving Image)

Reconstructed images at heartbeat time phases with an arbitrary time interval are created at different positions in a longitudinal direction of the object to be examined (Z-axis direction, i.e., slicing direction) in the above-described manner, and thus a tomogram of a whole heart at a heartbeat time phase with an arbitrary time interval, i.e., a three-dimensional image can be produced.

By displaying thus obtained three-dimensional images on the display device (see reference number 205 in FIG. 1) in order of heartbeat time phase, a three-dimensional cardiac moving image representing continuously and smoothly pulsing heart, i.e., a four-dimensional image can be obtained.

INDUSTRIAL APPLICABILITY

As described above in detail, according to the present invention, discontinuity of projection data in performing helical scans can be solved, whereby a good cardiac tomogram with few motion artifacts caused by heartbeat can be obtained.

Further, even when a phase difference is generated between an object's heartbeat cycle and a scan cycle of helical scan, the number of divided projection data and the data width can be properly adjusted, whereby a cardiac tomogram with few motion artifacts can be obtained. Further, a three-dimensional cardiac image at a heartbeat time phase with an arbitrary time interval can be created by creating reconstructed images in a heartbeat time phase with an arbitrary time interval at a plurality of different positions in the longitudinal direction of the object and gathering the reconstructed images having the same heartbeat time phase in the longitudinal direction.

Further, by displaying thus obtained three-dimensional images on a display device in order of heartbeat time phase, a three-dimensional cardiac moving image representing continuously and smoothly pulsing heart, i.e., a four-dimensional image can be obtained.

What is claimed is:

1. A method of producing a cardiac tomogram using an X-ray CT apparatus performing helical scans which has multiple columns of X-ray detector in a slicing direction of an object to be examined and using projection data detected by the X-ray detector, comprising the steps of:

measuring electrocardiographic information of the object;

calculating a number of projection data to be divided necessary for reconstruction of a tomogram in each of the helical scan;

collecting divided projection data in an identical heartbeat time phase on the basis of the number of projection data to be divided and an electrocardiographic cycle obtained in the step of measuring the electrocardiographic information, and forming projection data necessary for reconstruction of a tomogram;

interpolating a discontinuous portion of the above formed projection data in the slicing direction of the object and forming continuous projection data; and forming a cardiac tomogram of the object using the continuous projection data.

2. A method of producing a cardiac tomogram according to claim 1, wherein in the step of finding the division number of projection data, the scan number making the scan cycle of helical scan in synchronism with the electrocardiographic cycle obtained by the electrocardiographic information is found and the division number of projection data necessary for reconstruction of tomograms at each scan in the synchronizing scan number is calculated.

3. A method of producing a cardiac tomogram according to claim 1 or 2, wherein the step of forming the continuous projection data includes interpolating means for interpolating the discontinuous portion of projection data in the slicing direction of the object by using projection data in 180-degree opposite relation and at an identical heartbeat time phase, and projection data continuous in the slicing direction of the object is formed by the interpolating means.

4. A method of producing a cardiac tomogram according to claim 1 or 2, wherein the step of forming the continuous projection data includes interpolation means for interpolating the discontinuous data in the slicing direction of the object by utilizing interpolation using projection data in the identical heartbeat time phase in the vicinity of the discontinuous portion, and projection data continuous in the slicing direction of the object is formed by the interpolating means.

5. A method of producing a cardiac tomogram using an X-ray CT apparatus according to claim 4, wherein projection data used in the interpolation is obtained by weighing projection data in an identical heartbeat time phase in the vicinity of the discontinuous portion.

6. A method of producing a cardiac tomogram using an X-ray CT apparatus according to claim 1 or 2, further including a step of finding a data width of the divided projection data, wherein projection data at an arbitrary heartbeat time phase and in a range of projection angle necessary for image reconstruction by adjusting at least any of a starting projection angle, the divided projection data number, and the data width.

7. A method of producing a cardiac tomogram using an X-ray CT apparatus according to claim 6, wherein the projection data in the projection angle range necessary for image reconstruction are formed by setting the data width of divided projection data wide, performing weighting processing on data close to a boundary of the respective divided projection data, and adding and superposing the boundary portion of adjoining divided projection data.

8. A method of producing a cardiac tomogram using an X-ray CT apparatus according to claim 6, wherein the projection data at an arbitrary heartbeat time phase is formed by changing a starting projection angle of the divided projection data.

9. A method of producing a cardiac tomogram using an X-ray CT apparatus according to claim 6, wherein a plurality of projection data respectively having different distances of the starting projection angle of the divided projection data by an arbitrary projection angle are formed, and a plurality of cardiac tomograms at a heartbeat time phase with an arbitrary time interval by image-reconstructing the plurality of projection data.

10. A method of producing a cardiac tomogram using an X-ray CT apparatus according to claim 9, wherein the step of forming a plurality of cardiac tomograms at a heartbeat time phase with an arbitrary time interval includes the steps of: performing weighing processing in the slicing direction of the object on the plurality of projection data necessary for image reconstruction found from the divided projection data; image-reconstructing the plurality of projection data which have been subjected to the weighing processing and obtaining a plurality of cardiac tomograms at different slicing positions; and performing interpolating processing of interpolation or extrapolation on the plurality of cardiac tomograms and obtaining a cardiac tomogram at an arbitrary slicing position.

11. A method of producing a cardiac tomogram using an X-ray CT apparatus according to claim 9, wherein the step of forming a plurality of cardiac tomograms at a heartbeat time phase with an arbitrary time interval includes the steps of: performing interpolation or extrapolation in the slicing direction on the plurality of projection data necessary for image reconstruction found from the divided projection data and obtaining arbitrary projection data; and image-reconstructing the arbitrary projection data and obtaining a cardiac tomogram at an arbitrary slicing position.

12. A method of producing a cardiac tomogram using an X-ray CT apparatus according to claim 6, wherein in the step of forming the continuous projection data, projection data at an arbitrary slicing position are formed from the collected divided projection data at a matching heartbeat time phase, and a moving image of cardiac section is obtained by forming cardiac tomograms from those projection data.

13. A method of producing a cardiac tomogram using an X-ray CT apparatus according to claim 6, wherein in the step of forming the continuous projection data, a plurality of projection data gathering in the slicing direction of the object are formed at each heartbeat time phase from the obtained cardiac tomogram in an arbitrary heartbeat time phase, and three-dimensional cardiac images are obtained from those projection data.

14. A method of producing a cardiac tomogram using an X-ray CT apparatus according to claim 13, wherein a three-dimensional cardiac moving image is obtained by displaying the three-dimensional images in order of heartbeat time phase.

15. A cardiac tomograph, being an apparatus having multiple lines of X-ray detector in the slicing direction of the object for forming a cardiac tomogram of the object using projection data obtained by performing helical scans and detected by the X-ray detector, comprising:

electrocardiographic information measuring means for measuring electrocardiographic information of the object;

means for finding a division number of projection data necessary for reconstruction of a tomogram in each scan of the helical scans;

projection data forming means for collecting divided projection data at an identical heartbeat time phase on the basis of the projection data division number and an electrocardiographic cycle measured by the electrocardiographic information measuring means and forming projection data necessary for reconstruction of a tomogram;

continuous data forming means for forming continuous projection data by interpolating a portion where the above-formed projection data is discontinuous in the slicing direction of the object;

image creating means for creating a cardiac tomogram of the object using the continuous projection data; and display means for displaying the above-formed tomogram.

16. A cardiac tomograph using an X-ray CT apparatus according to claim 1, wherein means for finding the division number of the projection data finds the scan number at which a scan cycle of the helical scans is synchronized with an electrocardiographic cycle of the object, and calculates a division number of projection data necessary for reconstruction of a tomogram at each of the synchronizing scans.

17. A cardiac tomograph using an X-ray CT apparatus according to claim 15 or 16, wherein the continuous projection data forming means includes interpolating means for interpolating the discontinuous portion of projection data in the slicing direction using projection data in 180-degree opposite relation and at the identical heartbeat time phase.

18. A cardiac tomograph using an X-ray CT apparatus according to claim 15 or 16, wherein the continuous projection data forming means includes interpolating means for interpolating the discontinuous potion of projection data in the slicing direction of the object with interpolation using projection data at the identical heartbeat time phase in the vicinity of the discontinuous portion.

19. A cardiac tomograph using an X-ray CT apparatus according to claim 18, wherein the projection data used in the interpolation is obtained by weighing projection data at the identical heartbeat time phase in the vicinity of the discontinuous portion.

20. A cardiac tomogram using an X-ray CT apparatus according to claim 15 and 16, wherein the continuous projection data forming means includes means for finding a data width of the divided projection data, and projection data at an arbitrary heartbeat time phase and in a projection angle range necessary for image reconstruction are obtained by adjusting at least any of a starting projection angle of the divided projection data, the divided projection data number, and the data width.

21. A cardiac tomograph using an X-ray CT apparatus according to claim 20, wherein the projection data in the projection angle range necessary for image reconstruction is formed by setting the data width of the divided projection data to be wide, performing weighing processing on data close to boundaries between the respective divided projection data, and adding and superposing the boundary portions of adjoining divided projection data.

22. A cardiac tomograph using an X-ray CT apparatus according to claim 20, wherein projection data at an arbitrary heartbeat time phase are formed by shifting the starting projection angle of the divided projection data.

23. A cardiac tomograph using an X-ray CT apparatus according to claim 20, wherein a plurality of cardiac tomograms at heartbeat time phases with an arbitrary time interval are formed by forming a plurality of projection data respectively having different distances of the starting projection angle of the divided projection data by an arbitrary projection angle, and a plurality of cardiac tomograms at heartbeat time phases with an arbitrary time interval by image-reconstructing the plurality of projection data.

24. A cardiac tomograph according to claim 23, wherein means for forming a plurality of cardiac tomograms in heartbeat time phases with an arbitrary time interval includes: means for performing weighing processing in the slicing direction of the object on the plurality of projection data found from the divided projection data and necessary for image reconstruction; means for image-reconstructing each of the plurality of projection data which have been subjected to the weighing processing and obtaining a plurality of cardiac tomograms at different slicing positions; and means for obtaining a cardiac tomogram at an arbitrary slicing position by performing interpolating processing using interpolation or extrapolation on the plurality of cardiac tomograms.

25. A cardiac tomograph using an X-ray CT apparatus according to claim 23, wherein means for forming a plurality of cardiac tomograms at heartbeat time phases with an arbitrary time interval includes means for obtaining an arbitrary projection data by performing interpolation or extrapolation in the slicing direction on the plurality of projection data found from the divided projection data and necessary for image reconstruction and means for image-reconstructing the arbitrary projection data and obtaining a cardiac tomogram at an arbitrary slicing position.

26. A cardiac tomograph using an X-ray CT apparatus according to claim 20, wherein the continuous projection data forming means obtains and displays a cardiac tomogram by forming projection data at an arbitrary slicing position from the collected divided projection data at a matching heartbeat time phase and forming a cardiac tomogram from those projection data.

27. A cardiac tomograph using an X-ray CT apparatus according to claim 26, wherein the continuous projection data forming means forms a plurality of projection data gathering in the slicing direction of the object at each heartbeat time phase from the obtained cardiac tomogram at an arbitrary heartbeat time phase, and obtains and displays a three-dimensional cardiac image from those projection data.

28. A cardiac tomograph using an X-ray CT apparatus according to claim 27, wherein a three-dimensional cardiac moving image is obtained by displaying the three-dimensional images in order of heartbeat time phase.

* * * * *